United States Patent [19]

Holtkamp

[11] Patent Number: Plant 5,603

[45] Date of Patent: Dec. 17, 1985

[54] AFRICAN VIOLET PLANT NAMED BALTIMORE

[75] Inventor: Reinhold Holtkamp, Isselburg, Fed. Rep. of Germany

[73] Assignee: Gessellschaftsvertrag uber die Ergindergemeinschaft "OPTI-MARA", Rees Haffen, Fed. Rep. of Germany

[21] Appl. No.: 568,443

[22] Filed: Jan. 5, 1984

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Koch

[57] ABSTRACT

A new and distinct cultivar of African violet named Baltimore characterized by its very compact growth habit, girl type leaves, wire-like flower stems each of which carries seven or more flowers, white flower color, with purple tinging at the center of each petal and around the edges of certain of the petals, very long lasting flowers which do not drop, and by its ability to be grown close together with other plants without leaf stretching.

1 Drawing Figure

The present invention comprises a new and distinct cultivar of African violet plant, botanically known as *Saintpaulia ionantha,* and named Baltimore.

The new cultivar was referred to during the breeding and selection process by the designation G 17/III, and is a product of a planned breeding program.

The new cultivar was originated from a cross made in a controlled breeding program in Isselburg, West Germany. The female, or seed parent was a cultivar designated D 150/4 Red white girl. The male, or pollen parent was a cultivar designated 3/78 Violet.

The new cultivar Baltimore was discovered and selected by me as a flowering plant within the progeny of the stated cross in a controlled environment in Isselburg, West Germany. Asexual reproduction of the new cultivar by leaf cuttings and by division of shoots, as performed by me at Isselburg, West Germany, has demonstrated that the combination of characteristics as herein disclosed for the new cultivar are firmly fixed and are retained through successive generations of asexual reproduction.

Baltimore has not been observed under all possible environmental conditions. The phenotype may vary significantly with variations in environment such as temperature, light intensity and day length. The following observations, measurements and values describe the new cultivar as grown in Isselburg, West Germany, and Nashville, Tenn. under greenhouse conditions which closely approximate those generally used in commercial practice.

The following traits have been repeatedly observed and are determined to be basic characteristics of Baltimore, which in combination distinguish this African violet as a new and distinct cultivar:

1. Very compact growth habit.
2. Girl type leaves, with bright green center and surrounding dark green foliage color.
3. Seven to nine wire-like flower stems, each of which carries 7 or more flowers.
4. Leaf petioles do not stretch when plants are grown close together.
5. Very long lasting flowers which do not drop.
6. White flower color, with purple tinging at the center of each petal and around the edges of certain of the petals, providing a white-purple variegated appearance.

The accompanying photographic drawing shows a typical specimen plant of the new cultivar. The colors appearing in the photograph are as true as possible with color illustrations of this type.

In the following description, color references are made to The Royal Horticultural Society Colour Chart (R.H.S), except where general colors of ordinary significance are referred to. Color values were taken under natural light conditions at approximately midday on December 1 in Nashville, Tenn.

Botanical classification: *Saintpaulia ionantha,* Ramat. cv BALTIMORE.

Parentage:

*Male parent.*—3/78 Violet.

*Female parent.*—D 150/4 Red white girl.

Propagation: The new cultivar holds its distinguishing characteristics through successive propagations by leaf cuttings and by division of shoots.

Plant: From 6 cm. to 8 cm. tall when grown in pots, and approximately 16 cm. in diameter when fully grown.

Leaves.—General form: Round. Diameter: 55–60 mm. Texture: Velvety. Aspect: Shiny; hairy; light green center. Veins: Good visible light green; shiny. Color (upperside): Yellow green 147A. Color (underside): Yellow green 148D. Petiole: Short light green; hairy.

*Flowers.*—Buds: Ball shape. Sepals: Brownish. Color: Light green. Calyx: Flat funnel. Aspect: Spear shape, green tips. Peduncle: Light green to brownish.

*Individual flowers.*—Size: 30–35 mm. Color: White with purple centers, and, in certain petals, purple tinging on the edges. Upperside: Main color is white, tinged with purple Violet Group 82A–C. Underside: Main color is white, tinged with purple Violet Group 82A–C. Borne: On upright wire-like flower stems. Shape: Violet-shape, single; occasionally additional flower petal in the center. Flowering time: 11–12 weeks after potting.

*Reproductive organs.*—Anthers: 2 composed of 4 cells. Filaments: Light green ovary. Styles: Dark Purple.

*Roots.*—Whiten when young and active; brownish when older.

*Disease resistance.*—Good as experienced to date.

General observations: Baltimore is a very compact growing variety with girl type leaves. Plants can be grown very close together without stretching. Flower stems carry 7 and more single flowers from out of the center and form a compact head free above the leaves. Basic flower color is white, with deep purple centers and edging. Flowers are long lasting and will not drop.

I claim:

1. A new and distinct cultivar of African violet named Baltimore, as described and illustrated, and particularly characterized by its very compact growth habit, girl type leaves, wire-like flower stems each of which carries seven or more flowers, white flower color, with purple tinging at the center of each petal and around the edges of certain of the petals, very long lasting flowers which do not drop, and by its ability to be grown close together with other plants without leaf stretching.

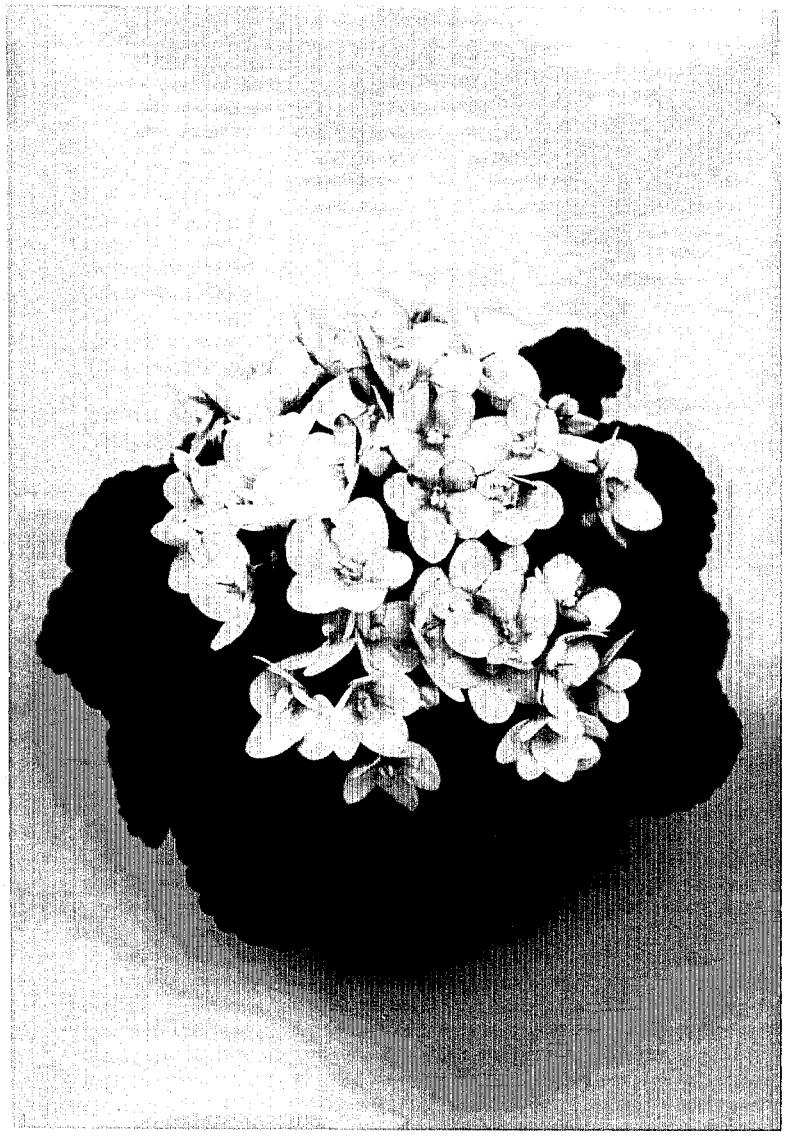

* * * * *